US011172955B2

United States Patent
Dayton et al.

(10) Patent No.: US 11,172,955 B2
(45) Date of Patent: Nov. 16, 2021

(54) ENDOSCOPY SYSTEM AND RELATED METHODS

(71) Applicant: Boston Scientific Scimed, Inc., Maple Grove, MN (US)

(72) Inventors: Peter L. Dayton, Brookline, MA (US); Katharine Eckerline, Boston, MA (US); Bryan Bannon, Duxbury, MA (US); Jeff Gray, Sudbury, MA (US); Barry Weitzner, Acton, MA (US); Bora Gumustop, Slingerlands, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 424 days.

(21) Appl. No.: 16/058,710

(22) Filed: Aug. 8, 2018

(65) Prior Publication Data

US 2019/0046223 A1 Feb. 14, 2019

Related U.S. Application Data

(60) Provisional application No. 62/543,238, filed on Aug. 9, 2017.

(51) Int. Cl.
*A61B 1/00* (2006.01)
*A61B 17/3203* (2006.01)
(Continued)

(52) U.S. Cl.
CPC ...... *A61B 17/3203* (2013.01); *A61B 1/00087* (2013.01); *A61B 1/00091* (2013.01); *A61B 1/00094* (2013.01); *A61B 1/015* (2013.01); *A61B 17/320016* (2013.01); *A61B 2017/0034* (2013.01); *A61B 2017/00296* (2013.01);
(Continued)

(58) Field of Classification Search
None
See application file for complete search history.

(56) References Cited

U.S. PATENT DOCUMENTS 4,628,940 A 12/1986 Naslund
5,630,795 A * 5/1997 Kuramoto .......... A61B 1/00068
600/153

(Continued)

FOREIGN PATENT DOCUMENTS

EP 2620110 A1 7/2013
JP 2013 085596 A 5/2013
(Continued)

*Primary Examiner* — Timothy J Neal
(74) *Attorney, Agent, or Firm* — Bookoff McAndrews, PLLC (57) ABSTRACT

According to one aspect, a medical device may include a shaft including a distal tip with a distal-facing surface. The shaft also may include a fluid lumen extending to the distal tip and a nozzle at a distal end of the fluid lumen. The nozzle may be configured to emit a fluid jet from the distal tip. The shaft also may include a vacuum lumen extending to the distal tip and a vacuum chamber at the distal tip. The vacuum lumen may open into the vacuum chamber, and the vacuum chamber may be wider than the vacuum lumen. The shaft may further include a vacuum opening, and the vacuum chamber may open into the vacuum opening. The vacuum opening may be defined by the distal-facing surface of the distal tip.

15 Claims, 7 Drawing Sheets

(51) Int. Cl.
*A61B 1/015* (2006.01)
*A61B 17/32* (2006.01)
*A61B 17/30* (2006.01)
*A61B 17/00* (2006.01)

(52) U.S. Cl.
CPC ............ *A61B 2017/00818* (2013.01); *A61B 2017/306* (2013.01); *A61B 2017/32032* (2013.01); *A61B 2017/320044* (2013.01); *A61B 2217/005* (2013.01); *A61B 2217/007* (2013.01)

(56) References Cited

U.S. PATENT DOCUMENTS

| | | | | |
|---|---|---|---|---|
| 5,976,073 | A * | 11/1999 | Ouchi | A61B 1/00089 600/129 |
| 6,375,635 | B1 * | 4/2002 | Moutafis | A61B 17/3203 604/22 |
| 6,572,578 | B1 * | 6/2003 | Blanchard | A61B 10/0266 604/22 |
| 7,115,100 | B2 | 10/2006 | McRury et al. | |
| 8,882,680 | B2 | 11/2014 | Furlong et al. | |
| 2002/0013570 | A1 * | 1/2002 | Ruegg | A61B 1/018 606/1 |
| 2004/0243157 | A1 * | 12/2004 | Connor | A61M 1/0084 606/159 |
| 2009/0326489 | A1 | 12/2009 | Kensy et al. | |
| 2013/0267891 | A1 * | 10/2013 | Malhi | A61M 25/0082 604/30 |

FOREIGN PATENT DOCUMENTS

| | | |
|---|---|---|
| WO | WO 00/56233 A1 | 9/2000 |
| WO | WO 2004/037095 A2 | 5/2004 |

* cited by examiner

ENDOSCOPY SYSTEM AND RELATED METHODS

CROSS-REFERENCE TO RELATED APPLICATION(S)

This patent application claims the benefit under 35 U.S.C. § 119 to U.S. Provisional Patent Application No. 62/543,238, filed on Aug. 9, 2017, the entirety of which is incorporated herein by reference.

TECHNICAL FIELD

The present disclosure relates generally to an endoscopy system and related methods. More specifically, this disclosure relates to an endoscopy system for treating tissue. The treatment may include, for example, performing an endoscopic necrosectomy as a therapy for pancreatic necrosis.

BACKGROUND

Endoscopic necrosectomy is a procedure for the surgical excision of necrotic tissue, and may be used to diagnose and treat patients with pancreatitis or patients with underlying pancreatic necrosis. Endoscopic necrosectomy may be performed using a reusable endoscope designed to support multiple, and sometimes different, diagnostic and therapeutic procedures. In some instances, a general use endoscope may not be optimized for a particular procedure. The advent of disposable endoscopes makes optimization around one specific procedure, or one specific type of procedure, feasible.

SUMMARY

Examples of the present disclosure relate to, among other things, an endoscopy system and related methods. Each of the examples disclosed herein may include one or more of the features described in connection with any of the other disclosed examples.

In one aspect of the present disclosure, a medical device may include a shaft including a distal tip with a distal-facing surface. The shaft also may include a fluid lumen extending to the distal tip and a nozzle at a distal end of the fluid lumen. The nozzle may be configured to emit a fluid jet from the distal tip. The shaft also may include a vacuum lumen extending to the distal tip and a vacuum chamber at the distal tip. The vacuum lumen may open into the vacuum chamber, and the vacuum chamber may be wider than the vacuum lumen. The medical device may further include a vacuum opening, and the vacuum chamber may open into the vacuum opening. The vacuum opening may be defined by the distal-facing surface of the distal tip.

In other aspects of the present disclosure, the medical device may include one or more of the features below. The vacuum chamber may be defined by one or more walls that extend parallel to a central longitudinal axis of the shaft. The vacuum opening may be defined by one or more edges, and at least one of the one or more edges may extend parallel to an edge of the distal-facing surface of the distal tip. One end of the vacuum chamber may be defined by a wall that extends parallel to the distal-facing surface of the distal tip, and the wall may be proximal of the distal-facing surface. The nozzle may be configured to emit the fluid jet across the vacuum opening. The nozzle may be configured to emit the fluid jet at an angle less than 90 degrees from the distal-facing surface of the distal tip. The nozzle may be configured to emit the fluid jet in a proximal direction. The nozzle may be configured to aim the fluid jet at one or both of the vacuum opening or the vacuum lumen. The nozzle may be configured to aim the fluid jet towards at least one of a central longitudinal axis of the vacuum lumen and a central longitudinal axis of the shaft.

In another aspect of the present disclosure, a medical device may include a shaft including a distal tip with a distal-facing surface. The distal tip also may include a protrusion extending distally from the distal-facing surface and a fluid lumen extending distally beyond the distal-facing surface through the protrusion. The distal tip may also include a nozzle at a distal end of the fluid lumen. The nozzle may be configured to emit a fluid jet from the protrusion. The distal tip may further include a vacuum opening defined by the distal-facing surface.

In other aspects of the present disclosure, the medical device may include one or more of the features below. The protrusion may extend parallel to a central longitudinal axis of the shaft. The protrusion may be cylindrical with a rounded distal end. The protrusion may be more flexible than the distal-facing surface. The nozzle may be configured to angle the fluid jet towards the vacuum opening. The protrusion may be more flexible than the distal-facing surface. The medical device may include a vacuum chamber at the distal tip. A vacuum lumen may open into the vacuum chamber. The vacuum chamber may be wider than the vacuum lumen. The vacuum chamber may extend to the vacuum opening. The nozzle may be configured to angle the fluid jet away from a central longitudinal axis of the protrusion and towards a central longitudinal axis of the vacuum lumen. The nozzle may be configured to direct the fluid jet proximally from a distal end of the protrusion towards the vacuum opening.

In yet another aspect of the present disclosure, a method for treating tissue may include inserting a distal tip of a medical device into a body lumen. The inserted medical device may include a shaft with a distal tip. The distal tip of the medical device may include a distal-facing surface and a protrusion extending distally from the distal-facing surface. The distal tip may also include a fluid lumen extending distally beyond the distal-facing surface through the protrusion. A nozzle may be at a distal end of the fluid lumen and the nozzle may be configured to emit a fluid jet from the protrusion. The distal tip may further include a vacuum opening defined by the distal-facing surface. The method may also include emitting the fluid jet at tissue and applying a suction force through the vacuum opening to suction tissue and fluid.

In other aspects of the present disclosure, the medical device may include one or more of the features below. The method may include dislodging tissue using the protrusion. Dislodging the tissue may include fragmenting the tissue with the fluid jet emitted from the protrusion, and engaging the tissue with an outer surface of the protrusion.

It may be understood that both the foregoing general description and the following detailed description are exemplary and explanatory only and are not restrictive of the claimed features. As used herein, the terms "comprises," "comprising," "includes," "including," or any other variation thereof, are intended to cover a non-exclusive inclusion, such that a process, method, article, or apparatus that comprises a list of elements does not have only those elements, but may have other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure, and together with the description, serve to explain the principles of the disclosure.

DETAILED DESCRIPTION

Figure 1:
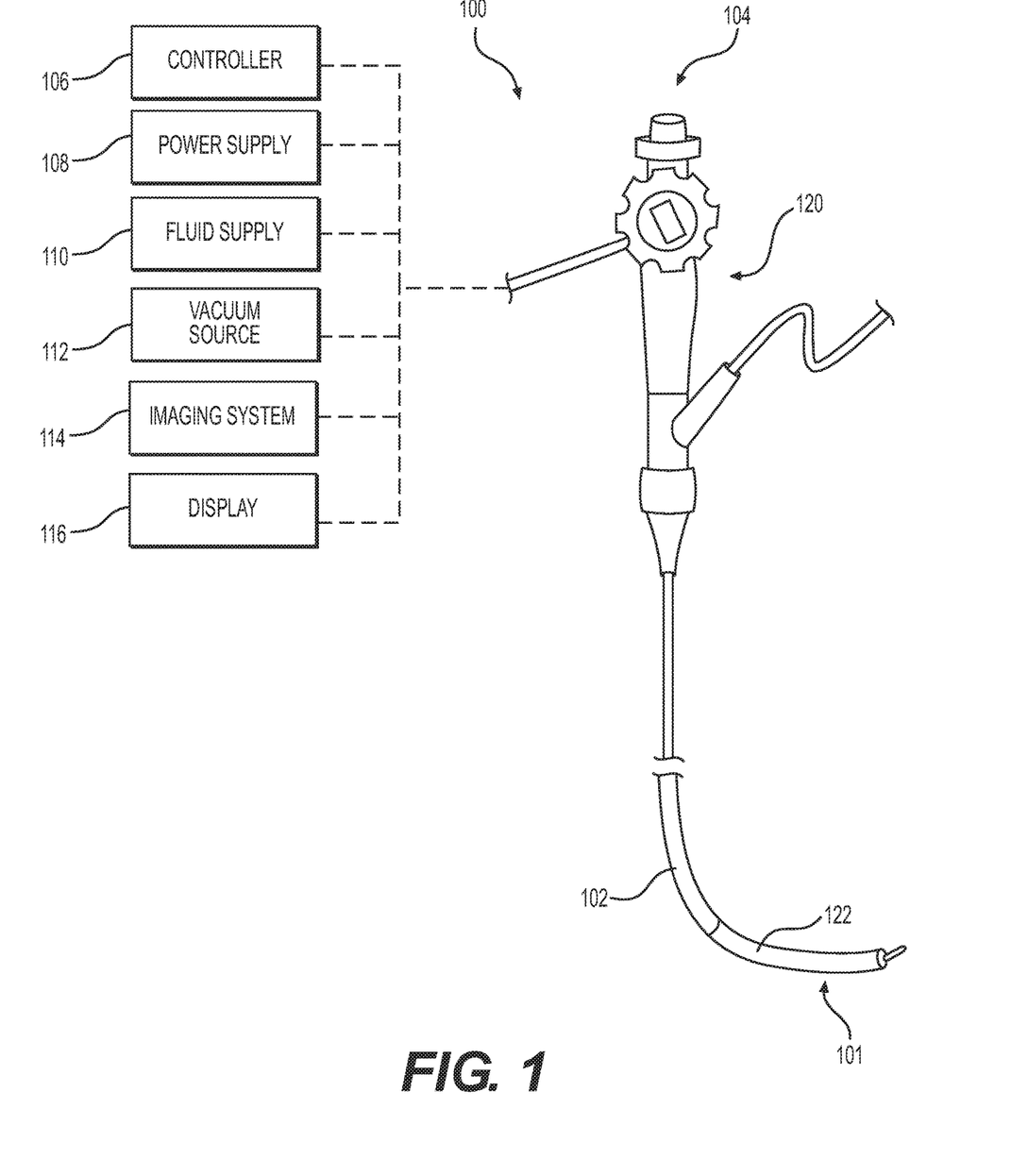
FIG. 1 illustrates an endoscopy system, according to an exemplary embodiment of the present disclosure.

The present disclosure is drawn to an endoscopy system for treating tissue, including performing an endoscopic necrosectomy as a treatment for infected pancreatic necrosis. An exemplary endoscopy system 100 is shown in FIG. 1. Endoscopy system 100 may include an endoscope 104. Endoscope 104 may include a handle assembly 120 and a flexible tubular shaft 102. The flexibility of shaft 102 may be sufficient to allow shaft 102 to bend, to facilitate navigation of shaft 102 through a subject's tortuous anatomical passages. Shaft 102 may terminate at a distal tip 101. Shaft 102 may include an articulation section 122 for deflecting distal tip 101 to provide for full retroflexion (e.g., rotation of distal tip 101 through an arc of 180 degrees) or only partial retroflexion (e.g., rotation of distal tip 101 through an arc of less than 180 degrees only). Endoscope 104 also may include one or more lumens extending therethrough, and one or more openings in communication with the one or more lumens. For example, the one or more lumens may extend through handle assembly 120 and/or shaft 102, and the one or more openings may be on handle assembly 120 and/or distal tip 101.

One or more auxiliary devices may be operatively coupled to endoscope 104. Exemplary auxiliary devices may include a controller 106, a power supply 108, a fluid supply 110, a vacuum source 112, an imaging system 114, and a display 116, each of which is briefly described below. Controller 106 may include, for example, any electronic device capable of receiving, storing, processing, generating, and/or transmitting data according to instructions given by one or more programs. Controller 106 may be operatively coupled to, or part of, one or more of endoscope 104 and the outer auxiliary devices, to control one or more aspects of their operation. Power supply 108 may include any suitable power source, and associated connectors, for supplying electronic components in the auxiliary devices and endoscope 104 with electrical power. Fluid supply assembly 110 may include a reservoir or a medical irrigation bag, a pump, and any suitable connectors (not shown). The pump may supply pressurized pulses of fluid to endoscope 104, and those pulses may be emitted from distal tip 101. Vacuum source 112 may provide suction or vacuum pressure to one or more of the endoscope lumens, and thereby provide a suction force at one or more of the endoscope openings, for capturing, positioning, and/or removing fluids, debris, tissue samples, and the like. Imaging system 114 may include imaging electronics to, for example, process signals received from an image sensor in endoscope 104, send signals for controlling the image sensor, adjust illumination levels of areas being viewed by the image sensor, and/or facilitate the display of patient data on display 116.

Figure 2:
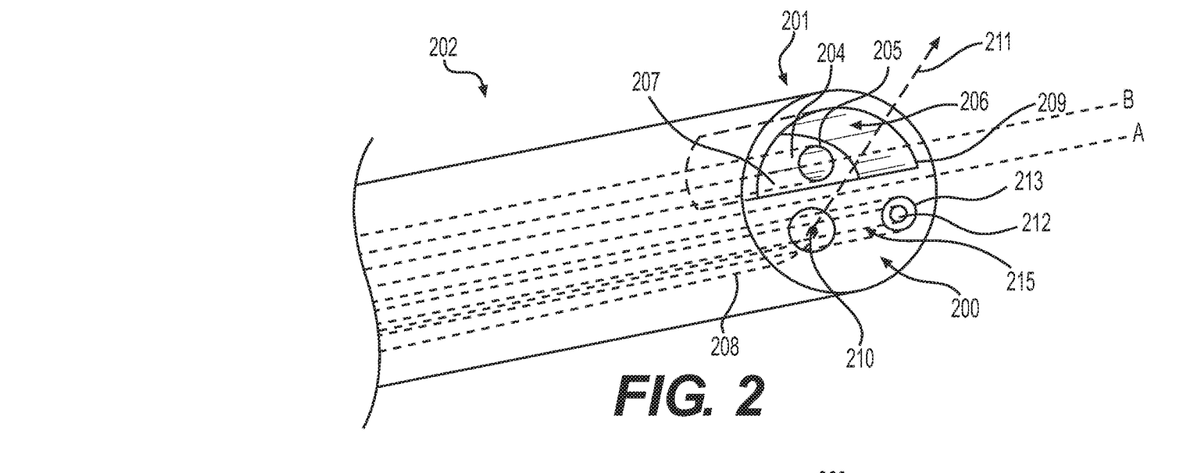
FIG. 2 illustrates a perspective view of a distal end of an endoscope, according to exemplary aspects of the present disclosure.

FIG. 2 illustrates an exemplary shaft 202 that may be used in an endoscope, such as endoscope 104. Shaft 202 may include a distal tip 201. Distal tip 201 may include a front or distal-facing wall 200. Wall 200 may be circular (as shown), square, triangular, rectangular, or any other shape. Wall 200 may include one or more openings therein that may be in fluid communication with one or more lumens in shaft 202.

Shaft 202 may include a vacuum lumen 204 extending therethrough. Vacuum lumen 204 may be in fluid communication with a vacuum source, such as vacuum source 112 of FIG. 1. Vacuum lumen 204 may terminate distally at an opening 205 on a wall 207. Wall 207 may be recessed in a proximal direction from wall 200. Opening 205 may open into a vacuum chamber 206 in distal tip 201. Vacuum chamber 206 may have a depth in the proximal-distal direction equal to a distance between walls 200 and 207. Vacuum chamber 206 may terminate distally at an opening 209 in wall 200.

In one example, vacuum chamber 206 and opening 209 may have a semicircular shape, with a curved side 216 and a straight side 217. Curved side 216 and straight side 217 may be defined by surfaces of distal tip 201 that extend parallel to a central longitudinal axis A of distal tip 201. In other examples, the surfaces may be angled towards or away from a central longitudinal axis B of vacuum lumen 204. It is also contemplated that vacuum chamber 206 and/or opening 209 may be circular, rectangular, triangular, square, and/or any other shape. For example, vacuum chamber 206 and/or opening 209 may have a shape similar to the shape of one of the halves of wall 200.

The vacuum source may create vacuum pressure in vacuum lumen 204, thereby creating a suction force in opening 205, vacuum chamber 206, and opening 209. The suction force may assist with collection and/or removal of necrotic tissue, debris, and fluid from a target area during a necrosectomy procedure. The material may be removed from the target area via vacuum lumen 204, or may be captured in vacuum chamber 206 and/or opening 209 and deposited in an area for removal by other means. Additionally or alternatively, the suction force may provide a user with the ability to grasp and hold tissue that is being treated, and then by moving distal tip 201, exert a force to position the tissue. Healthy tissue is less likely to be affected (e.g., damaged) by the suction force because of the tissue's strength and flexibility, while necrotic tissue, which is weaker, may be more likely to fragment. As such, the healthy tissue may be grasped, positioned, and released by distal tip 201 without being damaged, thereby providing a less traumatic way to manipulate tissue than mechanical means like clamps, forceps, barbs, and the like.

Shaft 202 also may include a fluid lumen 208 extending therethrough. Fluid lumen 208 may be in fluid communication with a fluid supply, such as fluid supply 110 of FIG. 1. Fluid lumen 208 may run parallel to or alongside vacuum lumen 204 and/or central longitudinal axis A. A fluid jet nozzle 210 may be at a distal end of fluid lumen 208 to direct fluid flowing through fluid lumen 208 outward from wall 200. Fluid jet nozzle 210 may include an opening at or adjacent wall 200. Fluid jet nozzle 210 may include a plain-orifice nozzle, shaped-orifice nozzle, surface-impingement single-fluid nozzle, pressure-swirl single-fluid spray nozzle, solid-cone single-fluid nozzle, compound nozzle, or any other suitable type of nozzle. In one example, fluid jet nozzle 210 may protrude from wall 200, such that the opening of fluid jet nozzle 210 may be distally offset from wall 200. For example, fluid jet nozzle 210 may include a semispherical bulge protruding from wall 200, with the opening of fluid jet nozzle 210 being positioned on a surface of the bulge.

Fluid jet nozzle 210 may direct and/or modify the fluid flowing through fluid lumen 208 to emit a fluid jet 211 outward from wall 200. In some examples, fluid jet 211 may be in the form of a stream of pressurized fluid, or a fan of pressurized fluid, in the shape of a cylinder, cone, triangle, spiral, and/or any other shape or pattern. Additionally or alternatively, a distal portion of fluid lumen 208 and/or fluid jet nozzle 210 may be curved or otherwise angled towards vacuum chamber 206 such that fluid jet nozzle 210 may emit fluid jet 211 towards an area distal and/or adjacent to vacuum chamber 206. In such an example, fluid jet 211 would follow a path that is angled relative to, but not perpendicular to, wall 200. Alternatively, fluid lumen 208 and/or fluid jet nozzle 210 may be straight so as to emit fluid jet 211 towards an area distal to fluid lumen 208, such that fluid jet 211 follows a path perpendicular to wall 200. Additionally or alternatively, a diameter of fluid lumen 208 and/or fluid jet nozzle 210 may decrease proximate to or at wall 200. In one example, a diameter of fluid jet nozzle 210 may be less than a diameter of a proximal portion of fluid lumen 208.

While fluid lumen 208 and fluid jet nozzle 210 are shown as being integral with shaft 202 and distal tip 201, it is contemplated that fluid lumen 208 and fluid jet nozzle 210 may be part of a separate instrument (e.g., a catheter) slidably movable through shaft 202, to extend distally from and retract proximally into wall 200. The user may extend, retract, rotate, and/or pivot the instrument to aim fluid jet 211 at a target area, without moving shaft 202 and distal tip 201.

Shaft 202 also may include an imaging lumen 215 extending therethrough. Imaging lumen 215 may receive imaging and/or illuminating components operatively coupled to imaging system 114. Imaging lumen 215 may terminate in distal tip 201 at an opening 213 on wall 200. Imaging lumen 215 may house components of an imaging assembly 212 including, for example, one or more imaging sensors, lenses, and or illumination elements. An exemplary imaging sensor may be any sensor that detects light and conveys information to allow for remote viewing of an image, such as CMOS or CCD sensors. An exemplary illumination element may emit any type of light to illuminate the area proximate to the image sensor(s). The illumination element may include, for example a light source (e.g., an LED) and/or a light transmission cable (e.g., a fiber optic cable). Imaging lumen 215 and/or opening 213 may angle the image sensor and/or the illumination element to provide a viewing angle that is tilted toward vacuum chamber 206 and/or fluid jet nozzle 210, to help the user see the target area being treated. For example, a central axis of a field of view of the image sensor and/or the beam of light emitted by the illumination element may be angled toward vacuum chamber 206 and/or fluid jet nozzle 210. It is also contemplated that opening 213 of imaging lumen 211 may be located proximate an outer edge of wall 200 to provide a wider viewing angle for the user.

Figure 3:
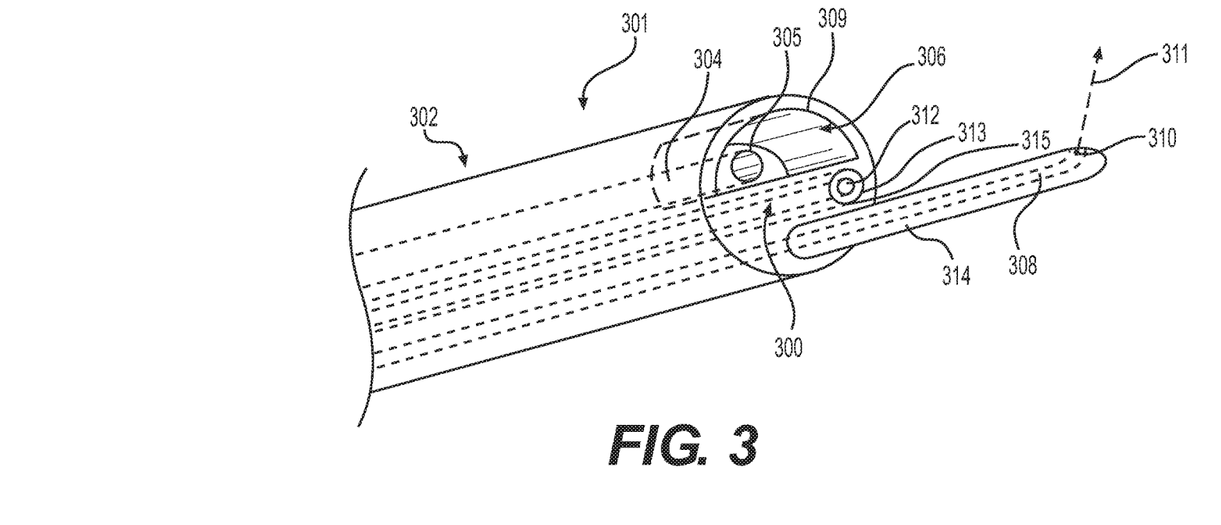
FIG. 3 illustrates a perspective view of another distal end of an endoscope, according to exemplary aspects of the present disclosure.

FIG. 3 illustrates another exemplary shaft 302 that may be used in an endoscope, such as endoscope 104 (see FIG. 1). Similar to shaft 202 shown in FIG. 2, shaft 302 may include a distal-facing wall 300, a vacuum lumen 304, an opening 305, a vacuum chamber 306, an opening 309, a fluid lumen 308, an imaging lumen 315, an opening 313, and an imaging assembly 312. Shaft 302 also may include a protrusion 314 extending distally from wall 300. In one example, protrusion 314 may have a central longitudinal axis extending parallel to, or alongside, the central longitudinal axis of distal tip 301, such that protrusion 314 extends perpendicularly from wall 300. Alternatively, the central longitudinal axis of protrusion 314 may be non-parallel to the central longitudinal axis of distal tip 301, such that protrusion 314 extends at a non-perpendicular angle from wall 300.

Protrusion 314 may have a cylindrical shape. Alternatively, protrusion 314 may have a square cross-sectional shape, a pronged configuration similar to a fork with splines, a hook shape, or any other suitable shape. The distal tip of protrusion 314 may be rounded, or otherwise blunt, for engaging tissue being treated, to facilitate separating necrotic tissue from healthy tissue without harming the healthy tissue. In one example, protrusion 314 may be made of a soft material that may be capable of pivoting, flexing, bending, and/or otherwise deflecting, when forced against tissue. For example, protrusion 314 may be made of silicone, polyurethane, or any other soft material. Protrusion 314 may, for example, be made of any material softer and/or more flexible than the material forming wall 300 (and/or the material supporting wall 300). As such, protrusion 314 may be used to wipe off necrotic tissue using, for example, the rounded tip of protrusion 314 and/or a radially-outward facing lateral surface of protrusion 314. Alternatively, protrusion 314 may be at least partially rigid. The flexibility/rigidity of protrusion 314 may be selected based on the characteristics of the tissue being treated, to ensure that necrotic tissue may be fragmented or otherwise manipulated by protrusion 314, while healthy tissue may remain undamaged.

Fluid lumen 308 may extend through protrusion 314, and may be similar to fluid lumen 208 shown in FIG. 2. Fluid lumen 308 may lead to a fluid jet nozzle 310, similar to fluid jet nozzle 210 shown in FIG. 2, located at a distal tip of protrusion 314. A fluid jet 311 emitted from fluid jet nozzle 310 may be angled relative to fluid lumen 308. For example, fluid jet 311 may be angled towards vacuum chamber 306, such that fluid jet 311 passes through an area distal and/or adjacent to vacuum chamber 306. In another example, fluid jet 311 may be aligned with the central longitudinal axis of protrusion 314.

It is contemplated that the direction of travel of fluid jet 311 may be adjusted by bending or otherwise manipulating protrusion 314. Manipulating protrusion 314 may include forcing protrusion 314 against tissue to bend protrusion 314. Additionally or alternatively, protrusion 314 may be independently controlled by the user using steering wires or similar components to deflect protrusion 314. Protrusion 314 may be deflected independently of distal tip 301.

While fluid lumen 308 and fluid jet nozzle 310 are shown as being integral with shaft 302 and distal tip 301, it is contemplated that fluid lumen 308 and fluid jet nozzle 310 may be part of a separate instrument (e.g., a catheter) slidably movable through shaft 302 to extend distally from and retract proximally into wall 300. The user may extend, retract, rotate, and/or pivot the instrument to aim fluid jet 311 at a target area, without moving shaft 302 and distal tip 301.

Figure 4:
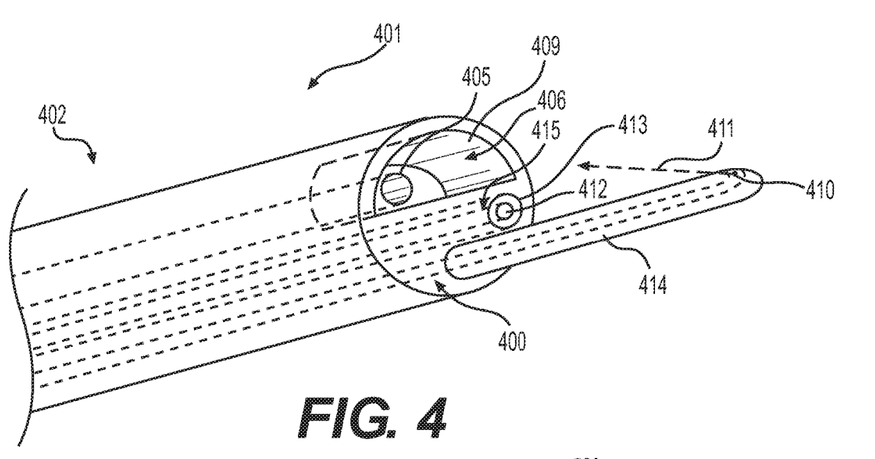
FIG. 4 illustrates a perspective view of another distal end of an endoscope, according to exemplary aspects of the present disclosure.

FIG. 4 illustrates another exemplary shaft 402 that may be used in an endoscope, such as endoscope 104 (see FIG. 1). Similar to shaft 302 shown in FIG. 3, shaft 402 may include a distal-facing wall 400, a vacuum lumen 404, an opening 405, a vacuum chamber 406, an opening 409, a fluid lumen 408, an imaging lumen 415, an opening 413, an imaging assembly 412, a protrusion 414, and a fluid jet nozzle 410 emitting a fluid jet 411. Fluid jet nozzle 410 may aim fluid jet 411 into vacuum chamber 406 and/or opening 409, including straight into opening 405. This may ensure that the fluid is immediately evacuated from the target area instead of pooling therein. Additionally or alternatively, fluid jet 411 may have a higher velocity than fluid jet 211 and/or fluid jet 311, to disrupt tissue in the region between protrusion 414 and vacuum chamber 406 with a greater force. The higher velocity fluid jet 411 may have a higher fluid flow rate, resulting in a greater volume of fluid being introduced into the target area. Aiming the higher velocity fluid jet 411 toward vacuum chamber 406 may assist with evacuation of the additional fluid and may protect non-targeted tissue by giving the high velocity jet a "backstop" or hard surface to absorb the force of the jet and prevent collateral tissue damage.

Figure 5:
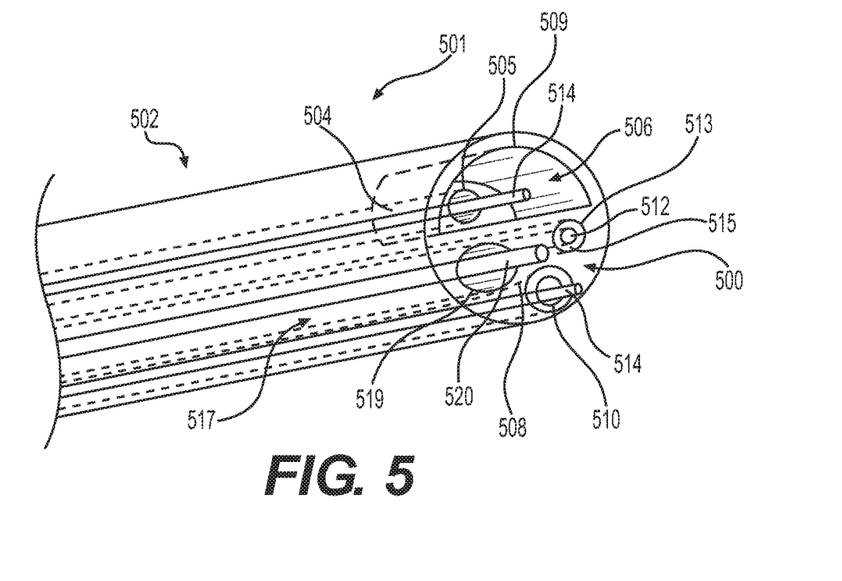
FIG. 5 illustrates a perspective view of another distal end of an endoscope, according to exemplary aspects of the present disclosure.

FIG. 5 shows another exemplary shaft 502 that may be used in an endoscope, such as endoscope 104 (see FIG. 1). Similar to endoscope 202 shown in FIG. 2, shaft 502 may include a distal-facing wall 500, a vacuum lumen 504, an opening 505, a vacuum chamber 506, an opening 509, a fluid lumen 508, a fluid jet nozzle 510 an imaging lumen 515, an opening 513, and an imaging assembly 512. Vacuum lumen 504, fluid lumen 508, fluid jet nozzle 510, opening 505, and/or any other lumen and/or opening in shaft 502 and distal tip 501 may receive one or more auxiliary instruments 520. It also is contemplated that fluid lumen 508 and fluid jet nozzle 510 may be part of a protrusion (not shown), similar to protrusions 314 or 414 shown in FIGS. 3 and 4. Instruments 520 may be routed through the one or more lumens to emerge from the one or more openings, where the instruments 520 may be extended distally and retracted proximally relative to wall 500. In one example, shaft 502 may include an additional instrument lumen 517 terminating at an opening 519 at wall 500, for receiving instrument 520. The one or more lumens may have a reinforced surface or coating therein to protect shaft 502 from damage resulting from passing instruments 520 therethrough. Instruments 520 may include one or more of a snare, a basket, forceps, a grasper, a vibrational tool, a stiffer tool, or any other suitable tool.

Figure 6A:
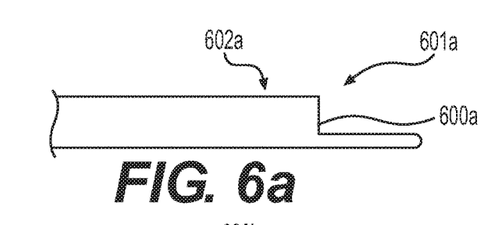
FIGS. 6A and 6B illustrate side profile views of distal ends of two endoscopes, according to exemplary aspects of the present disclosure.
Figures 6B, 7:
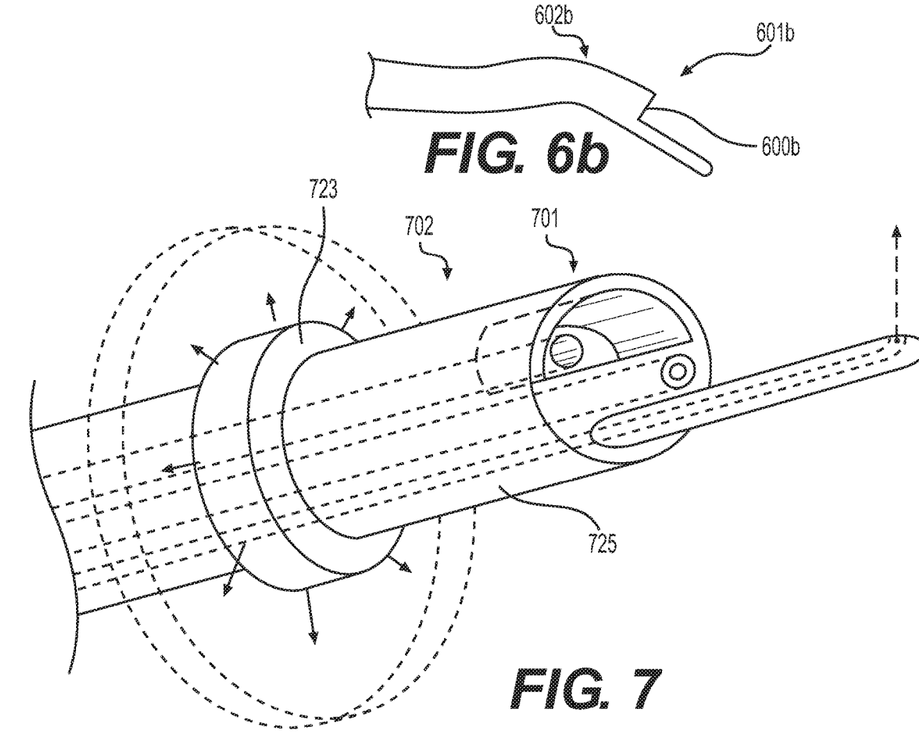
FIG. 7 illustrates a perspective view of another distal end of an endoscope, according to exemplary aspects of the present disclosure.

FIGS. 6A and 6B illustrate two examples of shafts 602a, 602b and distal tips 601a, 601b of an endoscope, such as endoscope 104 (see FIG. 1). Distal tip 601a has a straight section 621a leading up to a distal-facing wall 600a. Distal tip 601b has a pre-curved section 621b leading up to a distal-facing wall 600b. Pre-curved section 621b may curve distal tip 601b such that its central longitudinal axis may be angled at approximately 45, 90, 135, or 180 degrees, or any other suitable angle, relative to a proximal portion of shaft 602b. Pre-curved section 621b may assist the user with navigating through body lumens of a patient and/or reaching necrotic tissue during a procedure. Any of the previously described examples of shafts may have pre-curved section 621b. Pre-curved section 621b also may be utilized in combination with any of the aforementioned articulation sections.

FIG. 7 shows an exemplary shaft 702 having a distal tip 701, similar to shaft 302 and distal tip 301 of FIG. 3. A ring element 723 may surround a portion of shaft 702. Ring element 723 may be proximal from the distalmost end of shaft 702, proximate to distal tip 701 and/or the front wall 700 of distal tip 701. Ring element 723 may be positioned at any portion of endoscope 104, distal tip 701, shaft 702, or be incorporated into any of the previously described endoscope embodiments. Ring element 723 may be coupled to a radially-outward facing surface 725 of shaft 702. Ring element 723 may form a seal with surfaces of an anatomical lumen or other opening at a target area into which distal tip 701 may be inserted. Additionally or alternatively, ring element 723 may form a seal with surfaces of a stent holding open an opening or passage at a target area through which distal tip 701 is inserted. In some examples, multiple spaced-apart ring elements may be present to provide multiple seals.

In one example, ring element 723 may inflate or otherwise expand to form the seal (shown in dotted lines in FIG. 7), and may deflate or otherwise contract to facilitate removal of ring element 723 and shaft 702. Ring element 723 may expand radially-outwardly and contract radially-inwardly. Ring element 723 may include, for example, an annular balloon. In one exemplary use, ring element 723 may expand to form a seal in a passage (e.g., an aperture in tissue or a channel through a stent) from a subject's stomach into the subject's pancreas that allows access to a walled-off necrosis (WON). The sealing may plug up the WON, allowing the user to use chemicals, some of which may be caustic, to clean the WON, while preventing the chemicals from leaking out of the WON and into contact with the mucosa of the subject's gastrointestinal tract. Ring element 723 may be utilized on any of the aforementioned shafts.

Figure 9:
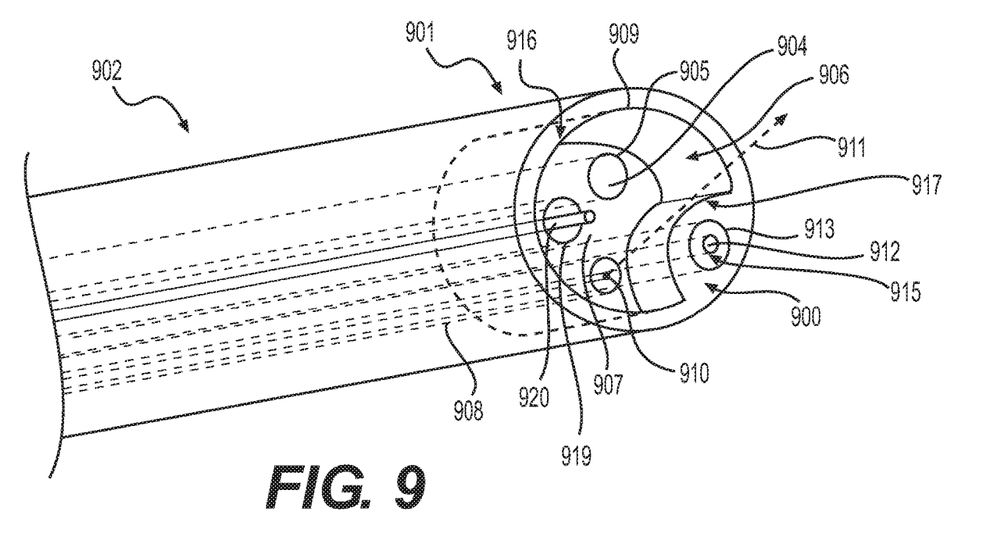
FIG. 9 illustrates a perspective view of another distal end of an endoscope, according to exemplary aspects of the present disclosure.

FIG. 9 shows another exemplary shaft 902 and distal tip 901 that may be used in an endoscope, such as endoscope 104 (see FIG. 1). Shaft 902 may include a distal-facing wall 900, a vacuum lumen 904, an opening 905, a vacuum chamber 906, an opening 909, a fluid lumen 908, a fluid jet nozzle 910, an imaging lumen 915, an opening 913, and an imaging assembly 912. Similar to the distal tip 201 of FIG. 2, distal tip 901 may include a wall 907 recessed in a proximal direction from wall 900. In some embodiments, opening 905 and/or fluid jet nozzle 910 may be present on wall 907. Distal tip 901 may also include a working lumen 918 within opening 919 present on wall 907. Instrument(s) 920 may be routed through working lumen 918 and may access the vacuum chamber 906. Instrument(s) 920 may be routed through working lumen 918 to emerge from opening 919, where the instrument(s) 920 may be extended distally and retracted proximally relative to wall 907. Opening 913 of imaging lumen 915 may be present on front wall 900 and may include an imaging assembly 912. Opening 909 may cover a substantial portion of the distal-facing wall 900. By having the opening 919 of the working lumen 918 present on recessed wall 907, material and/or debris suctioned by the vacuum lumen 904 may be easier to access with instrument(s) 920 because the material and/or debris may have a tendency to collect in the vacuum chamber 906 and proximate to the recessed wall 907. By providing the fluid jet nozzle 910 on recessed wall 907, the fluid jet 911 may be aimed at material and/or debris present in the vacuum chamber 906 and may assist with breaking apart that material and/or debris.

Opening 909 of distal tip 901 may include a curved portion 916 that is concavely curved toward the central longitudinal axis of distal tip 901 and may include a curved portion 917 that is convexly curved toward the central longitudinal axis of distal tip 901. In some examples, the imaging assembly 912 may be present on the recessed wall 907 (not shown) and/or any of the working lumen opening 919, vacuum lumen opening 905, and/or fluid jet nozzle 910 may be present on distal-facing wall 900. The vacuum lumen 904, vacuum chamber 906, fluid lumen 908, fluid jet nozzle 910, fluid jet 911, imaging lumen 915, imaging assembly 912, working lumen 918, tool 920, and/or any other component of distal tip 901 may include one or more of the features of any of the aforementioned embodiments described herein.

Figure 10:
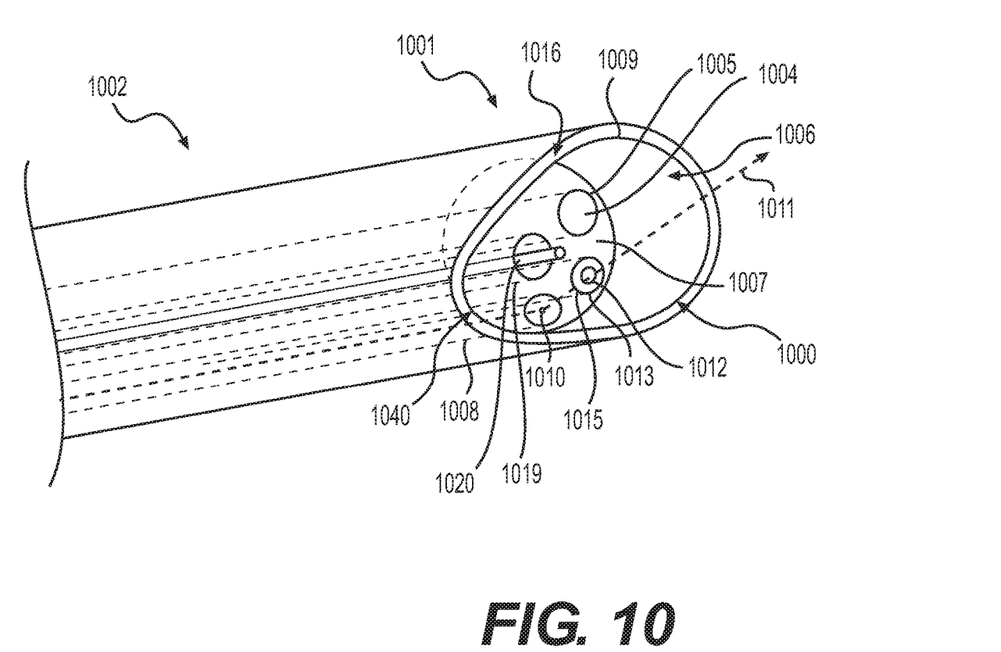
FIG. 10 illustrates a perspective view of another distal end of an endoscope, according to exemplary aspects of the present disclosure.

FIG. 10 shows another exemplary shaft 1002 and distal tip 1001 that may be used in an endoscope, such as endoscope 104 (see FIG. 1). Shaft 1002 may include a distal wall 1000, a vacuum lumen 1004, an opening 1005, a vacuum chamber 1006, an opening 1009, a fluid lumen 1008, a fluid jet nozzle 1010, an imaging lumen 1015, an imaging assembly 1012, and an opening 1013. Distal tip 1001 may also include a working lumen 1018 with an opening 1019 on a recessed wall 1007. Fluid jet nozzle 1010, opening 1005 of vacuum lumen 1004, opening 1013 of imaging lumen 1015, and opening 1019 of working lumen 1018 may be on recessed wall 1007. Instrument(s) 1020 may be routed through working lumen 1018 and opening 1019 to access the vacuum chamber 1006. Opening 1009 of vacuum chamber 1006 may include a proximal portion 1040 and a distal portion 1016. The proximal portion 1040 of the opening 1009 may be curved in the proximal direction such that the proximal portion 1040 is closer to recessed wall 1007 than the distal portion 1016. For example, the proximal portion 1040 may be flush with recessed wall 1007. In some examples, the vacuum chamber opening 1009 may include 20-40% of its circumference flush with or adjacent to recessed wall 1007, and the other 60-80% of its circumference may extend distally away from recessed wall 1007 and the proximal portion 1040. In one example, the openings 1005 and 1013 may be on a side of recessed wall 1007 that is closer to distal portion 1016. The proximal portion 1040, by virtue of dipping or being curved toward the proximal direction relative to the distal portion 1016, may assist in collecting material and/or debris in the vacuum chamber 1006, and/or may provide tool(s) 1020 and a water jet 1011 with easy access to material and/or debris drawn into vacuum chamber 1006. The vacuum lumen 1004, vacuum chamber 1006, fluid lumen 1008, fluid jet nozzle 1010, fluid jet 1011, imaging lumen 1015, imaging assembly 1012, working lumen 1018, tool(s) 1020, and/or any other component of distal tip 1001 may have one or more features of any of the aforementioned embodiments described herein.

Figure 8:
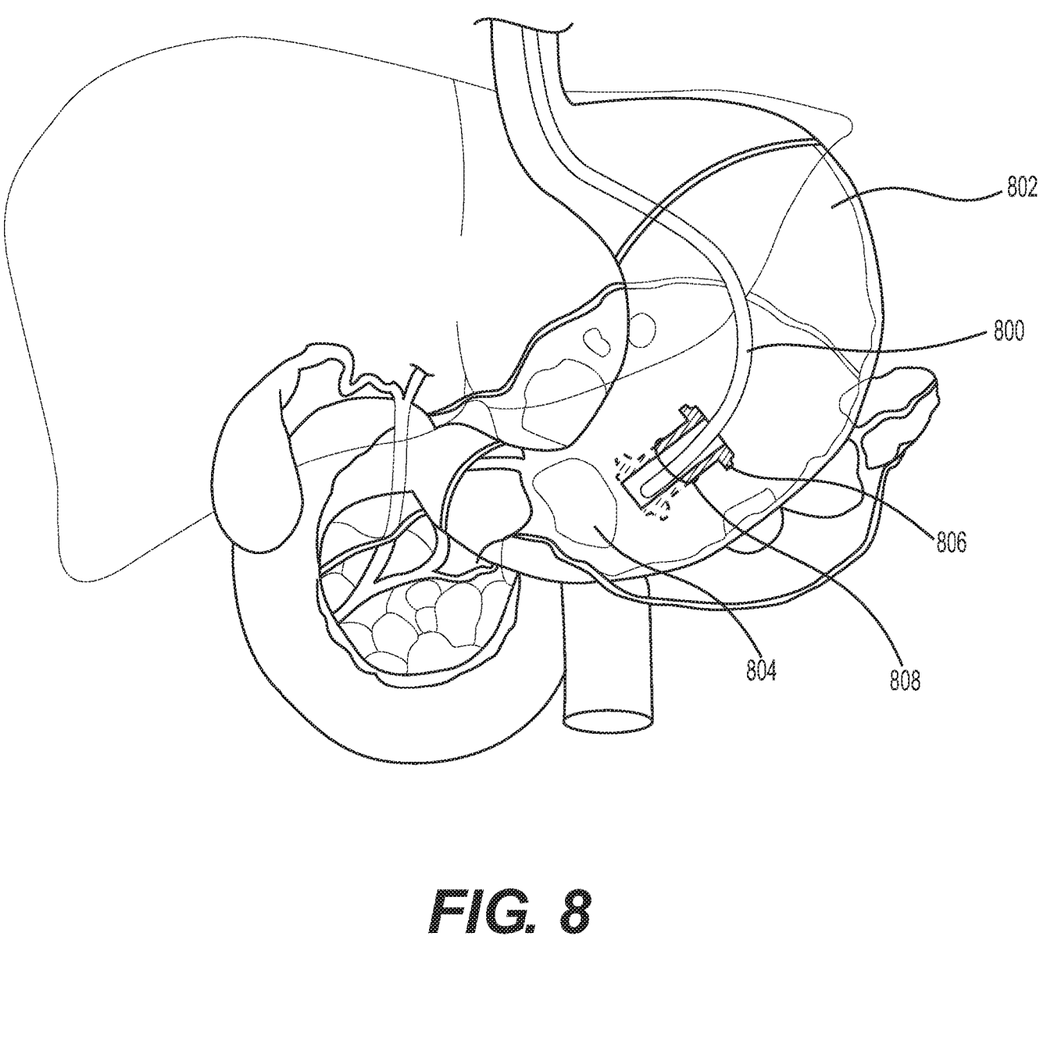
FIG. 8 illustrates a partial cross-sectional view of a subject's organs during performance of an endoscopic procedure, according to exemplary aspects of the present disclosure.

Each of the aforementioned endoscopes may be used to treat a host of ailments. One ailment that may be treated is acute pancreatitis complicated by necrosis of the pancreas or peripancreatic tissue. In such cases, a WON, which is a collection of liquid and/or solid necrotic debris in the pancreas, may be drained and cleaned out via endoscopic drainage and necrosectomy. As shown in FIG. 8, the user may locate a WON 804, obtain access into WON 804 by puncturing or otherwise creating an opening 808 through a wall of the subject's stomach 802 (or duodenum), and insert a stent 806 into opening 808 to keep it open, using any suitable methodologies known in the art. Stent 806 may be an AXIOS™ Stent, which may have flanged ends for holding tissue layers and a central passage for allowing drainage. An endoscope 800, which may be any of the aforementioned endoscopes, may be inserted through the subject's gastrointestinal tract, through stent 806, and to or into WON 804. Endoscope 800 may include a ring element, similar to ring element 723 of FIG. 7, for creating a seal between endoscope 800 and an internal surface of stent 806.

The user may use features of endoscope 800 to treat WON 804. For example, the user may use a suction force generated at the distal tip of endoscope 800 to grasp, position, fragment, and/or remove necrotic tissue from WON 804. The necrotic tissue may be withdrawn by suction through endoscope 800. Alternatively, the necrotic tissue may be grasped and drawn out of WON 804 and into stomach 802 (or duodenum) using the suction force, and dropped off in stomach 802 (or duodenum) by turning off the suction force. Additionally or alternatively, the user may use a high-pressure pulsed fluid jet emitted from the distal tip of endoscope 800 to break apart necrotic tissue, thereby facilitating its removal. The emitted fluid may be removed from the targeted area by the suction force. Additionally or alternatively, the user may use a finger-like protrusion at the distal tip of endoscope 800 to wipe away necrotic tissue, to facilitate its removal.

Figure 11:
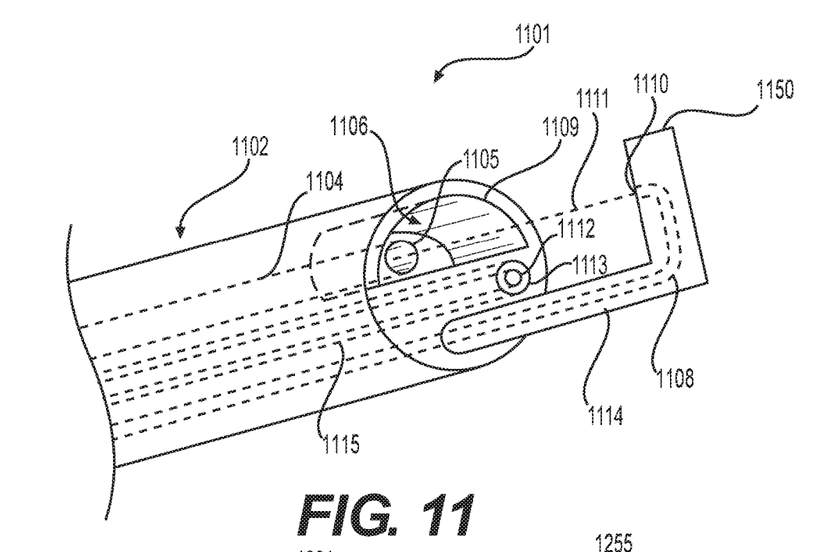
FIG. 11 illustrates a perspective view of another distal end of an endoscope, according to exemplary aspects of the present disclosure.

FIG. 11 shows another exemplary shaft 1102 and distal tip 1101 that may be used in an endoscope, such as endoscope 104 (see FIG. 1). It is contemplated that shaft 1102 and distal tip 1101 may have any feature, or combination of features, of the other exemplary shafts and distal tips described herein, and vice versa. in this example, shaft 1102 may include a vacuum lumen 1104, an opening 1105, a vacuum chamber 1106, an opening 1109, a fluid lumen 1108, a fluid jet nozzle 1110, an opening 1113, and an imaging assembly 1112. A protrusion 1114 may protrude distally from a distal-facing surface of distal tip 1101. Fluid lumen 1108 may extend through protrusion 1114, and may lead to fluid jet nozzle 1110. Protrusion 1114 may be angled or curved. For example, protrusion 1114 may be L-shaped and nozzle 1110 of fluid lumen 1108 may be positioned on a proximal-facing surface of protrusion 1114, such that water jet 1111 exiting nozzle 1110 may be directed into or otherwise toward vacuum chamber 1106. In one embodiment, nozzle 1110 may emit water jet 1111 into or otherwise toward opening 1105. In other examples, protrusion may be hook shaped and/or may be otherwise curved to facilitate a change of direction of the fluid from moving substantially distally to moving substantially proximally.

Nozzle 1110 may be positioned at a portion of protrusion 1114 proximate to an end or tip 1150 of protrusion 1114. The configuration of protrusion 1114, and of positioning of nozzle 1110 on protrusion 1114, may protect fragile tissue the user would not like to contact water jet 1111, such as the fragile wall of the necrotic pouch, and may prevent undesired damage to tissue. For example, the space between end 1150 and nozzle 1110 may prevent water jet 1111 from contacting areas of tissue accidentally when a user is moving distal tip 1101. For example, end 1150 of protrusion 1114 may abut against a surface of tissue, preventing further movement of protrusion 1114 towards or into the tissue surface, thereby preventing waterjet 1111 from coming into contact with the tissue.

Water jet 1111 may be used to cut or otherwise separate portions of tissue, when, for example a user positions tissue in a gap between protrusion 1114 and the distal front face of distal tip 1101. When the user selectively moves tissue or other material into the gap (which may, for example, extend between the nozzle 1110 and the vacuum chamber 1106), the fluid jet 1111 may cut the tissue or other material with water jet 1111 without unwanted damage to surrounding tissue. When the tissue or other material is cut free, it may fall into the gap between protrusion 1114 and the distal front face of distal tip 1101, where it may be secured to distal tip 1101 by the suction force provided at opening 1109.

Figure 12:
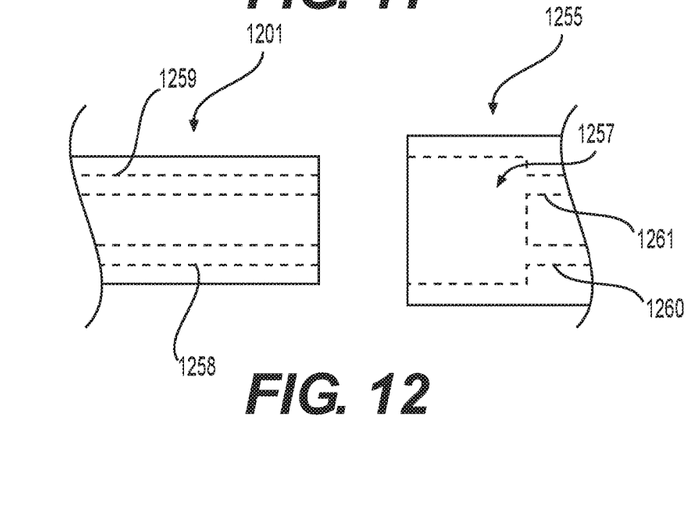
FIG. 12 illustrates a side view of a distal end of an endoscope and a proximal end of an end cap, according to exemplary aspects of the present disclosure.

FIG. 12 shows an exemplary side view an exemplary distal tip 1201 of an endoscope and an end cap 1255. End cap 1255 may include a chamber 1257 configured to receive distal tip 1201, such that end cap 1255 is secured to (e.g., over) distal tip 1201. In some examples, end cap 1255 may form a water-tight seal with distal tip 1201. For example, the inner surface(s) forming chamber 1257 may form a fluid tight seal with the exterior surface(s) of distal tip 1201. Distal tip 1201 of the endoscope may include a fluid lumen 1258 and a suction lumen 1259. End cap 1255 may include fluid lumen 1260 and suction lumen 1261, configured to align with fluid lumen 1258 and suction lumen 1259 of distal tip 1201, when end cap 1255 is coupled to distal tip 1201. The distal portion of end cap 1255 may include any of the fluid jet nozzle, suction chamber, imaging port, illumination port, working channel, and/or other features of any of distal tips 201, 301, 401, 501, 601, 701, 901, 1001, and 1101. Additionally or alternatively, any of distal tips 201, 301, 401, 501, 601, 701, 901, 1001, and 1101 may be implemented on a separate end cap that may then be coupled to the distal end of an endoscope or other shaft.

It also should be understood that one or more aspects of any of the endoscopes described herein may be used for cleaning or debris removal and/or fluid control in any part of the human body, such as for colonoscopies, examination of mucinous lesions, and/or other procedures where debris removal and/or fluid control are performed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method for treating tissue, the method comprising: inserting a distal tip of a medical device into a body lumen, wherein the medical device comprises:
    a shaft including the distal tip, the distal tip including:
        a distal-facing surface,
        a flexible protrusion extending distally from the distal-facing surface,
        a fluid lumen extending distally beyond the distal-facing surface through the protrusion,
        a nozzle at a distal end of the fluid lumen, wherein the nozzle is configured to emit a fluid jet from the protrusion, and
        a vacuum opening defined by the distal-facing surface,
    emitting the fluid jet at tissue;
    moving tissue using the protrusion, including bending the protrusion; and
    applying a suction force through the vacuum opening to suction tissue and fluid.

2. The method of claim 1, further comprising dislodging tissue using the protrusion.

3. The method of claim 2, wherein dislodging the tissue includes fragmenting the tissue with the fluid jet emitted from the protrusion, and engaging the tissue with an outer surface of the protrusion.

4. The method of claim 1, wherein the protrusion includes a dome-shaped distal end and a radially-outermost surface, radially-outward from a central longitudinal axis of the protrusion, wherein the radially-outermost surface extends from the distal-facing surface to the dome-shaped distal end.

5. The method of claim 1, wherein the protrusion is cylindrical.

6. The method of claim 1, wherein the nozzle is configured to angle the fluid jet towards the vacuum opening.

7. The method of claim 1, wherein the protrusion is more flexible than the distal-facing surface.

8. The method of claim 1, wherein the distal tip further comprises a vacuum chamber, wherein a vacuum lumen opens into the vacuum chamber, the vacuum chamber is wider than the vacuum lumen, and the vacuum chamber extends to the vacuum opening.

9. The method of claim 8, wherein the vacuum chamber is defined by one or more walls that extend parallel to a central longitudinal axis of the shaft.

10. The method of claim 1, wherein the nozzle is configured to angle the fluid jet away from a central longitudinal axis of the protrusion and towards a central longitudinal axis of the shaft.

11. The method of claim 1, wherein the nozzle is configured to direct the fluid jet proximally from a distal end of the protrusion towards the vacuum opening.

12. The method of claim 1, wherein the nozzle is configured to emit the fluid jet across the vacuum opening.

13. The method of claim 1, wherein the nozzle is configured to direct the fluid jet at an angle less than 90 degrees from the distal-facing surface of the distal tip.

14. The method of claim 1, wherein the nozzle is configured to emit the fluid jet in a proximal direction.

15. The method of claim 1, wherein the nozzle is configured to aim the fluid jet at the vacuum opening.

\* \* \* \* \*